(12) United States Patent
Zehner

(10) Patent No.: US 7,708,718 B2
(45) Date of Patent: May 4, 2010

(54) SYRINGE SHIELD

(76) Inventor: John A. Zehner, 7715 Loma Ct., Suite C, Fishers, IN (US) 46038

( * ) Notice: Subject to any disclaimer, the term of this patent is extended or adjusted under 35 U.S.C. 154(b) by 94 days.

(21) Appl. No.: 11/724,151

(22) Filed: Mar. 14, 2007

(65) Prior Publication Data
US 2007/0219505 A1 Sep. 20, 2007

Related U.S. Application Data

(60) Provisional application No. 60/783,360, filed on Mar. 17, 2006.

(51) Int. Cl.
*A61M 5/32* (2006.01)
(52) U.S. Cl. .................. 604/192; 604/193; 604/198
(58) Field of Classification Search .................. 604/72, 604/192, 193, 197, 227; 600/5
See application file for complete search history.

(56) References Cited

U.S. PATENT DOCUMENTS

| | | | | |
|---|---|---|---|---|
| 5,078,695 A * | 1/1992 | Farrar et al. ............ | 604/192 |
| 5,417,326 A * | 5/1995 | Winer ................... | 206/365 |
| 6,159,144 A * | 12/2000 | Angel et al. .............. | 600/5 |
| 6,162,198 A * | 12/2000 | Coffey et al. ............. | 604/198 |
| 6,614,040 B1 | 9/2003 | Zens | |
| 6,717,163 B2 | 4/2004 | Zens | |
| 6,797,973 B2 | 9/2004 | Zens | |
| 6,828,577 B2 | 12/2004 | Zens | |
| 6,939,330 B1 * | 9/2005 | McConnell-Montalvo et al. ............ | 604/197 |
| 7,014,622 B1 * | 3/2006 | Pressly et al. ............. | 604/110 |
| 7,351,227 B2 * | 4/2008 | Lemer .................... | 604/192 |
| 7,370,759 B2 * | 5/2008 | Hommann ................ | 206/365 |
| 2005/0065476 A1 * | 3/2005 | Jensen et al. ............. | 604/197 |
| 2005/0215956 A1 * | 9/2005 | Nerney ................... | 604/218 |
| 2005/0215958 A1 * | 9/2005 | Hawthorne ............... | 604/227 |
| 2007/0129591 A1 * | 6/2007 | Yanke et al. .............. | 588/16 |

\* cited by examiner

*Primary Examiner*—Kevin C Sirmons
*Assistant Examiner*—Maria E Doukas
(74) *Attorney, Agent, or Firm*—Taft Stettinius & Hollister LLP

(57) ABSTRACT

A radiation shielding syringe carrier comprising a top cap, a main body and a needle shield, all formed from a radiation dense material. The main body preferably includes a syringe shield shaped to be threadably engaged to the bottom of the carrier. Preferably a separate top cap and shipping cap are provided.

15 Claims, 6 Drawing Sheets

SYRINGE SHIELD

CROSS-REFERENCE TO RELATED APPLICATION

This application claims the benefit of U.S. Patent Application Ser. No. 60/783,360, filed Mar. 17, 2006, entitled "SYRINGE SHIELD", the disclosure of which is incorporated herein by reference.

FIELD

This invention relates to an apparatus for holding and shielding a syringe, and more particularly to an apparatus for holding and shielding a syringe while it is being dosed with radiopharmaceuticals and which may be used to administer such radiopharmaceuticals to a patient while the syringe remains shielded therein. The shield may be used with or without an automatic dose dispensing machine to fill syringes with hazardous materials, usually radioactive liquid including radiopharmaceuticals.

BACKGROUND

Radiopharmaceuticals are radioactive materials that are widely used in the diagnosis and treatment of various diseases and body disorders. Radiopharmaceuticals are typically injected into the body of a patient by means of a hypodermic syringe. The repeated exposure to radioactive materials may over time present serious health hazards to the person dosing and administering the injection. This hazard is a result of radiation emanating from radioactive material which is to be injected.

One of the exposure risks occurs during the dosing procedure occurs when a specialized dose is prepared from a larger storage container of the radiopharmaceuticals by drawing the dose from the storage container into a syringe and while manipulating the syringe to prepare it for injecting and injecting into the patient. For example, the technician's upper extremities can receive a significant dose of radiation during the time the syringe is unshielded.

Accordingly, what is needed is an apparatus, preferably an entirely self contained and shielded apparatus, that may be used to prepare doses of radiopharmaceutical medicines into syringes without requiring a technician to directly touch or be involved in the dosing procedure. What is further needed is a sub structure of such an apparatus that can receive a syringe and perform all the necessary operations to remove the dose from a larger storage container without the need for manual intervention from a technician.

SUMMARY OF THE INVENTION

It is an aspect of the present invention to provide a syringe shield that is made of radiation-resistant or dense material that shields the technician from radiation exposure while the hypodermic syringe is being dosed, carried, and/or otherwise manipulated. Non-limiting examples of such radiation dense materials include tungsten, lead, stainless steel, etc. as is well known in the art. It is another aspect of the present invention to provide a syringe shield that allows an appropriately measured dose if radiopharmaceuticals to be prepared automatically inside a shielded machine without requiring any direct contact with either the syringe being dosed or the storage containers for the radiopharmaceuticals. It is yet another aspect of the invention to provide such a shield that can receive a syringe and perform all the necessary operations to remove a radiopharmaceutical dose from a larger storage container without the need for manual intervention from a technician.

More specifically, it is an aspect of the invention to provide a syringe shield which allows the syringe to be filled and/or the injection of the syringe contents without compromising the shielding while the syringe remains in the syringe shield. Additionally it is an object of the invention to provide such a shield that allows easy removal of the syringe needle (whether inside a dosing machine or by a technician), easy changing of the needle, caps or other locking accessories for the syringe as desired, which lessens radiation exposure to technicians, patients or other personnel, and which allows the syringe to remain in the syringe shield during these operations. Another aspect of the invention is to provide a syringe shield which reduces the risk of a technician or other worker from accidentally depressing the syringe plunger while capping or closing or otherwise manipulating the shield.

Other aspects of the invention preferably include the ability of the shield to integrate with an automatic dose dispensing and syringe filling machine. In that embodiment, the shield is preferably designed to allow a dose dispensing machine to remove the empty syringe with a needle and needle cap from the shield, remove the needle cap, fill the syringe with liquid, replace the syringe back into the shield, and recap the needle automatically within an entirely shielded environment without requiring any unshielded interaction by the technician.

These and other aspects of the present invention will become apparent from the following description, the description being used to illustrate the preferred embodiment of the invention when read in conjunction with the accompanying drawings.

DETAILED DESCRIPTION

Figure 1:
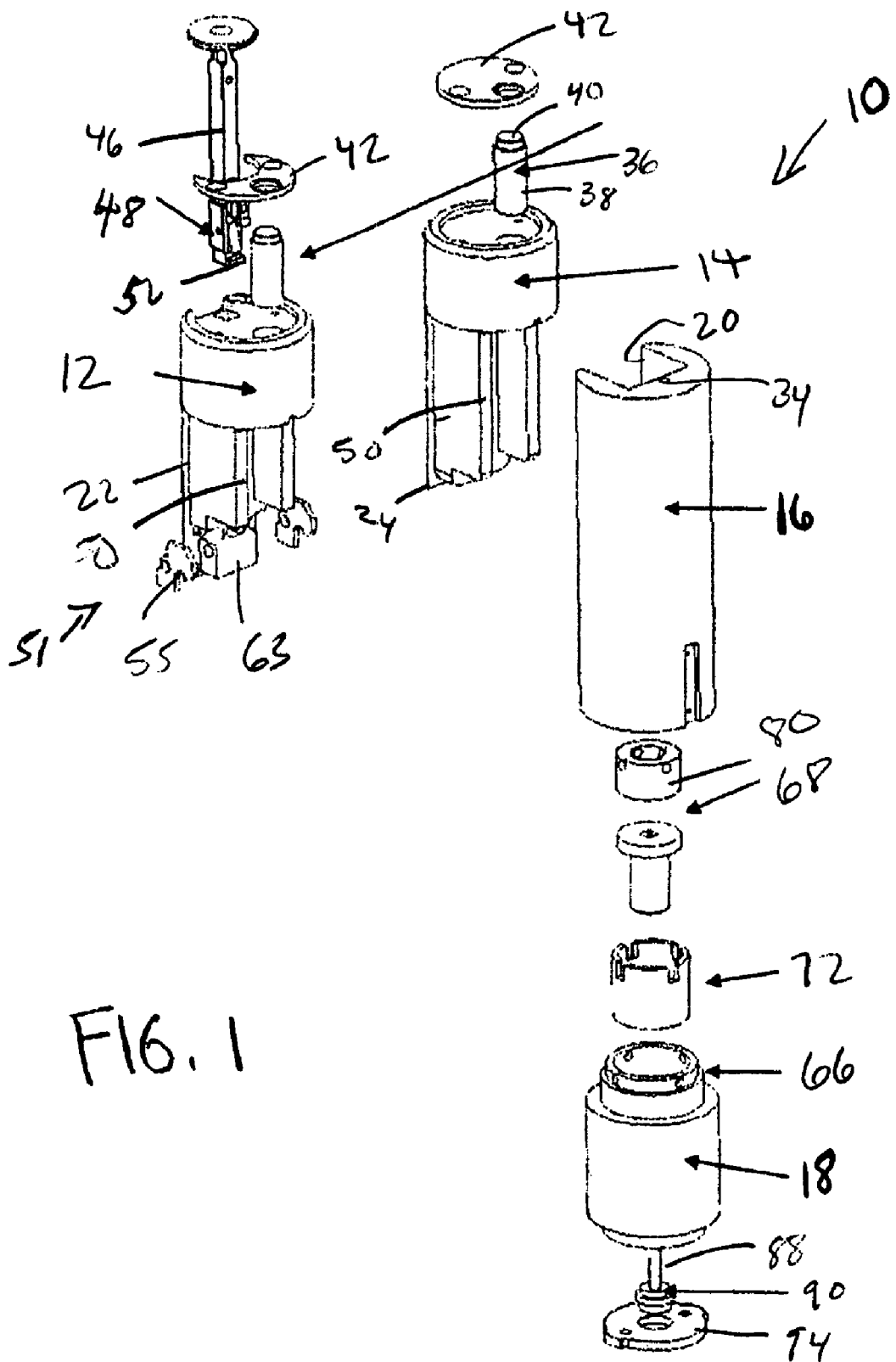
FIG. 1 is an exploded side perspective view of a syringe shield in accordance with the present invention.
Figure 2:
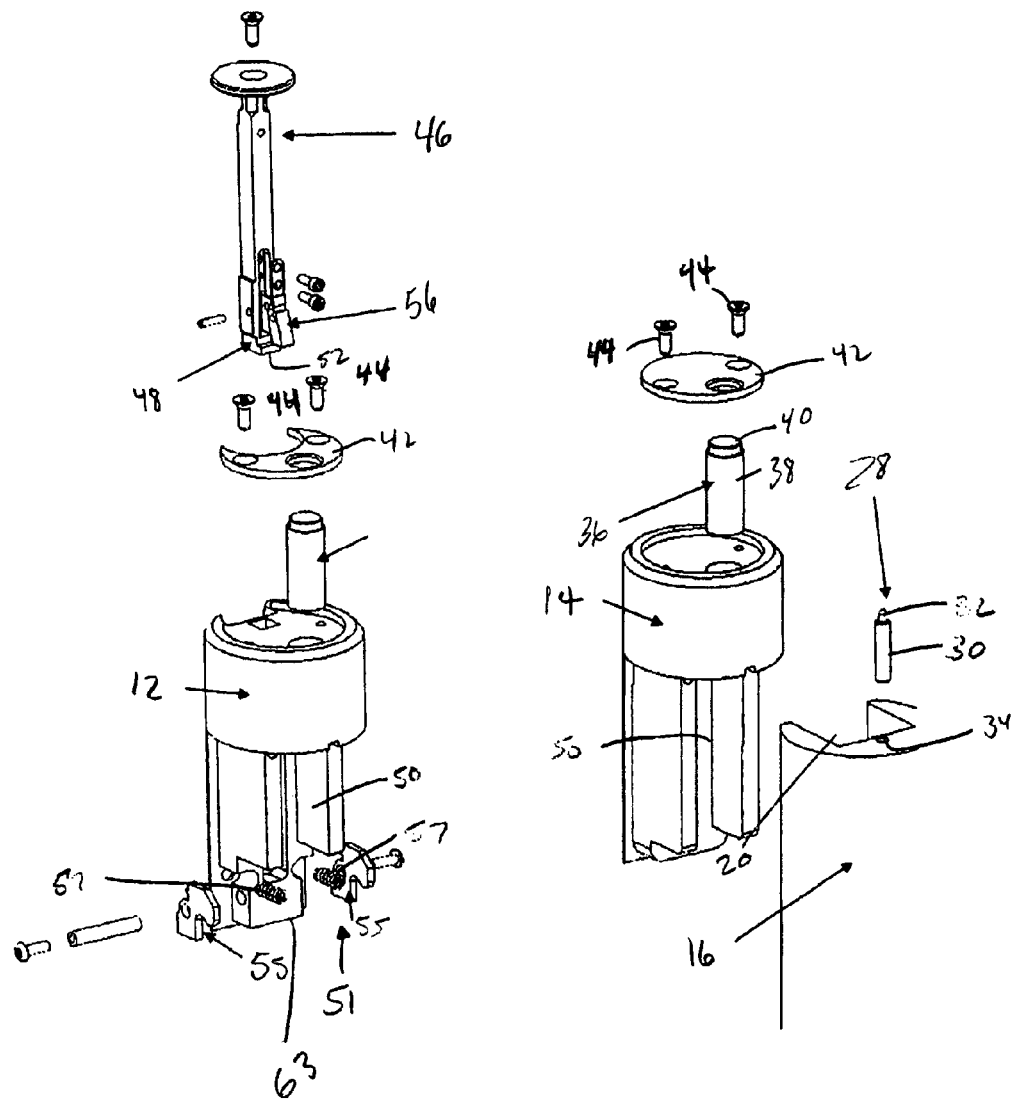
FIG. 2 is a detailed exploded side perspective view of a shipping cap and injecting cap for use in connection with the syringe shield of FIG. 1.
Figure 3:
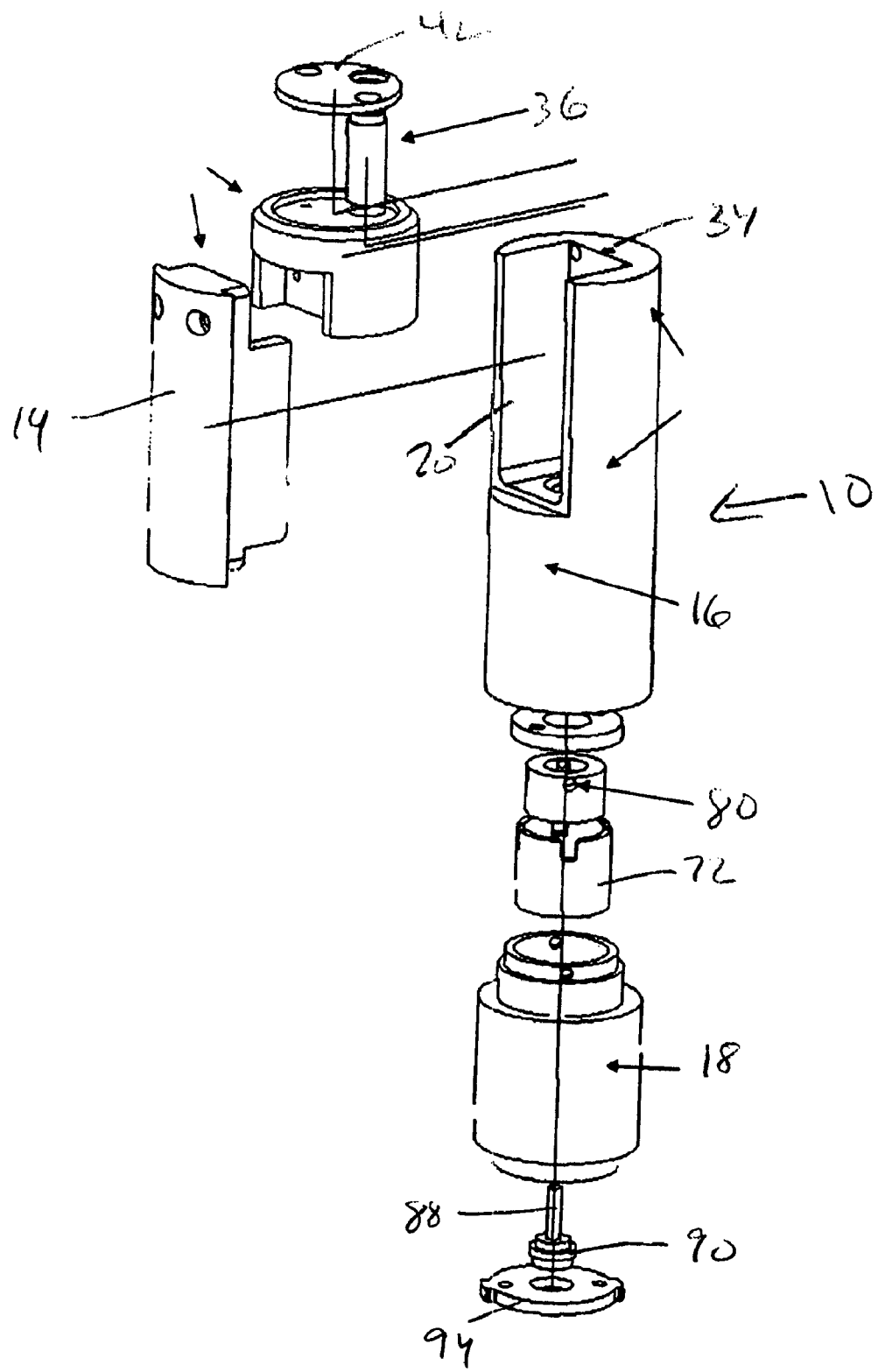
FIG. 3 is an exploded side perspective view of a syringe shield in accordance with the present invention shown from the opposite side of the syringe shield as shown in FIG. 1.
Figure 4:
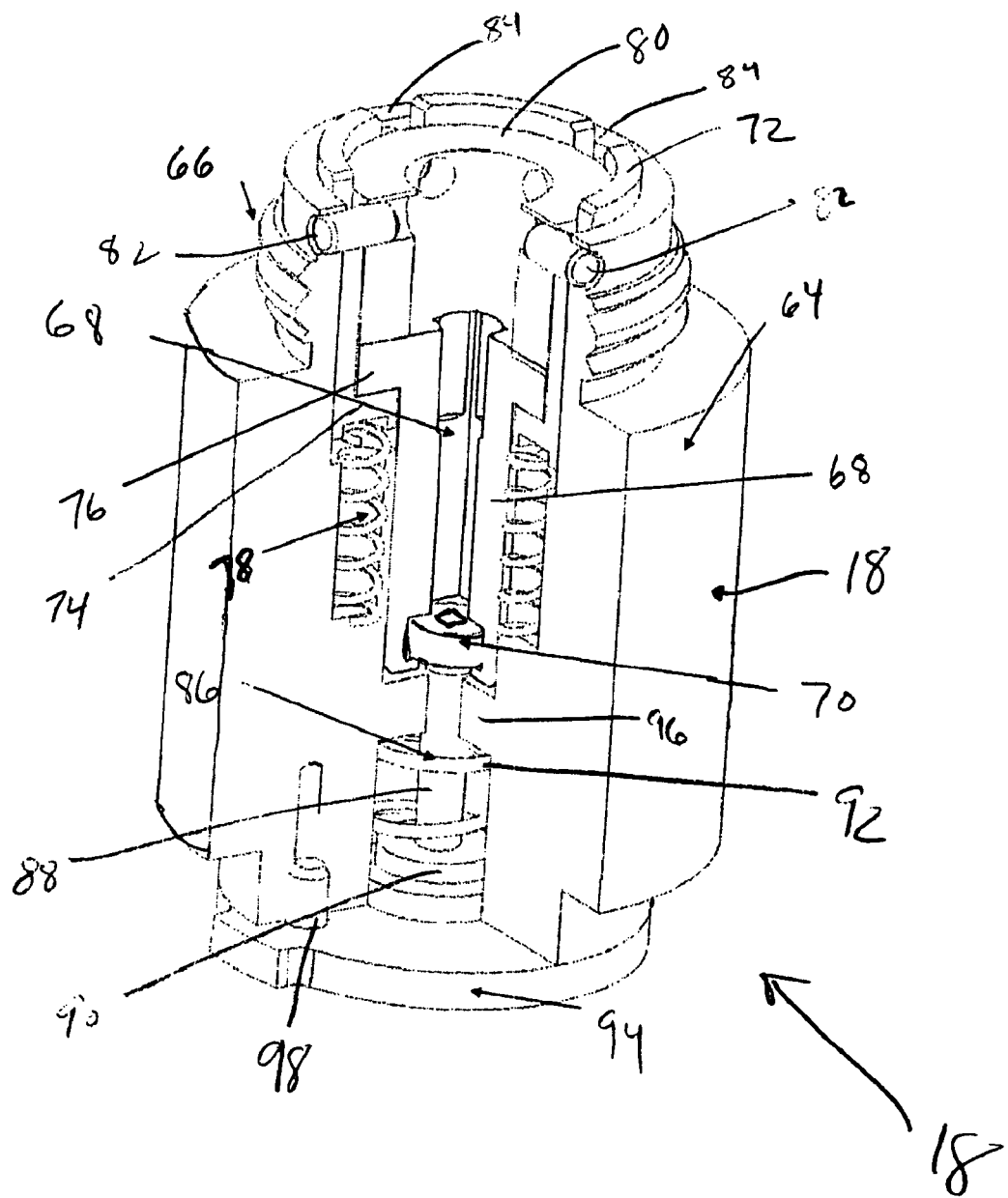
FIG. 4 is a cutaway side perspective view of the needle shield portion of the syringe shield as shown in FIG. 1.
Figure 5:
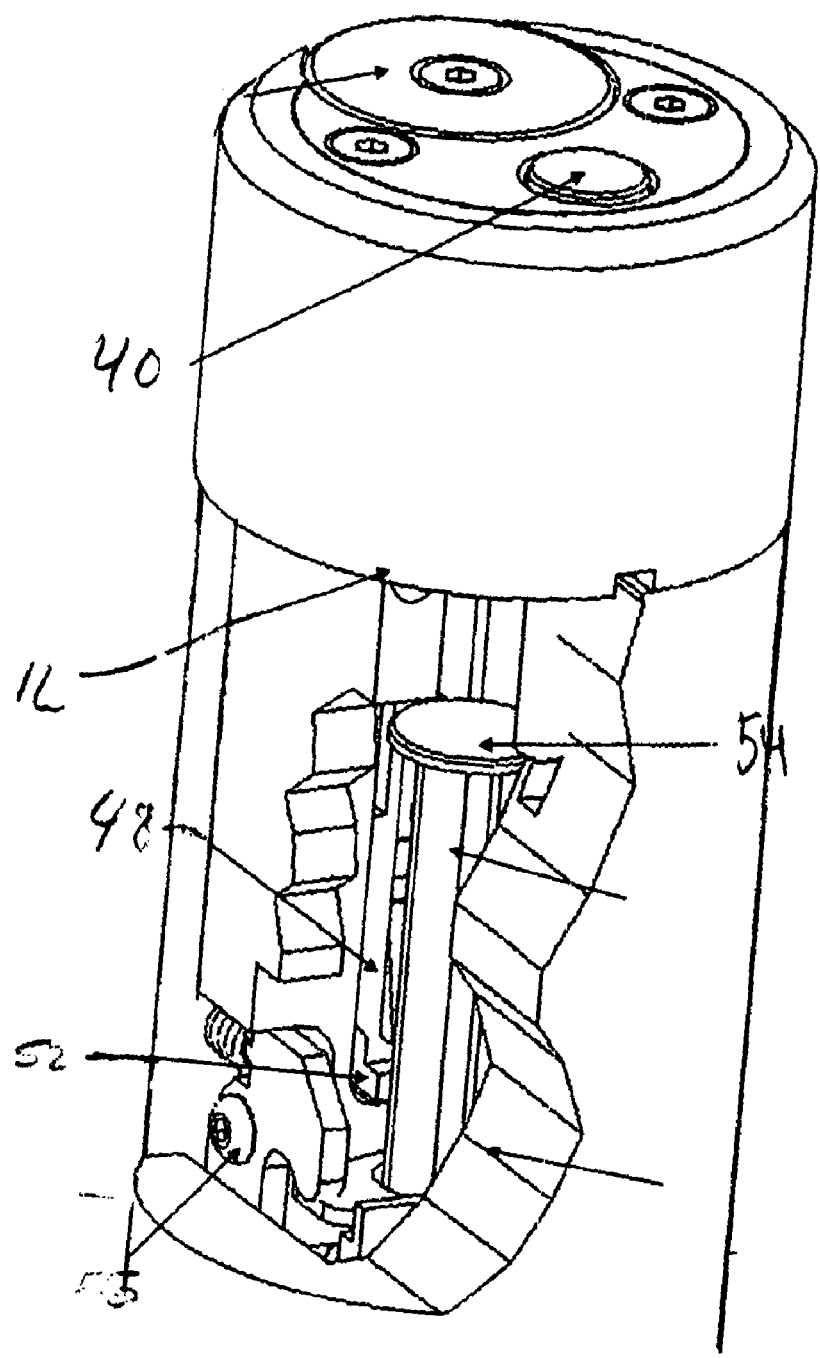
FIG. 5 is a cutaway side perspective view of the syringe shield of FIG. 1 having a syringe placed therein and having the injecting cap thereon in the park position.
Figure 6:
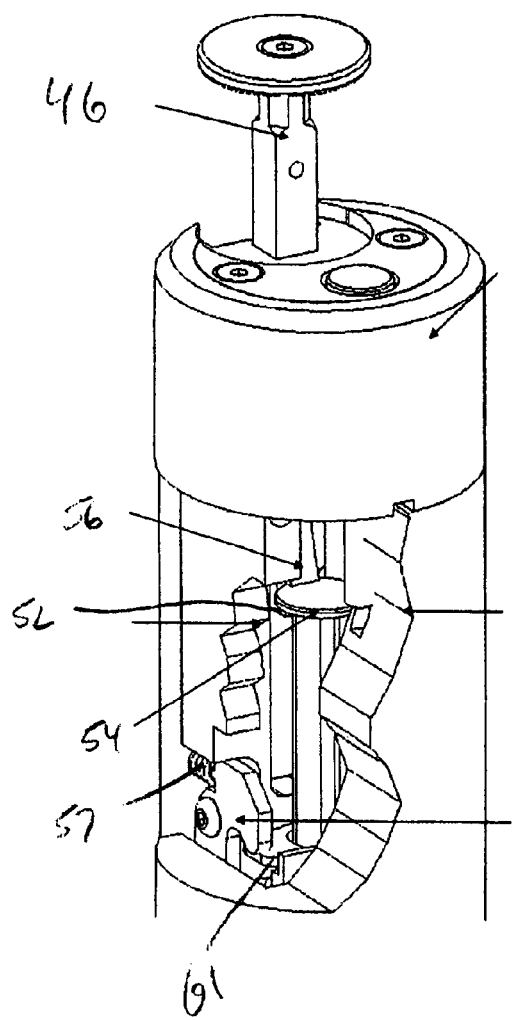
FIG. 6 is a cutaway side perspective view of the syringe shield of FIG. 5 having a syringe placed therein showing the plunger in a raised position.
Figure 7:
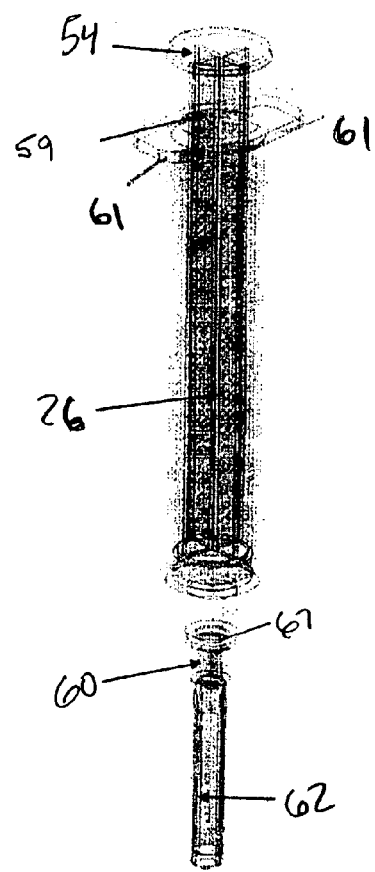
FIG. 7 is transparent perspective view of a syringe for use in connection with the syringe shield of FIG. 1.

As shown in above-identified FIGS. 1-7, and as will be discussed further herein, a syringe shield 10 in accordance with the present invention may include two separate caps, namely an injecting cap 12 and a shipping cap 14, a main body 16, and a needle shield 18. Preferably, the body 16 includes a side cutout portion 20 and the caps include corresponding downwardly extending projections 22, 24 which are shaped to cover the cutout portion 20 when the caps 12, 14 are engaged with the body 16. The side cutout 20 allows side access to the body 16 so that a syringe 26 may be placed in the body 16 more easily than in prior art top access only designs and because placing the caps 12, 14 on from the side makes it easier to avoid accidental plunging of the syringe 26 when the caps 12, 14 are placed on the body 16. More specifically, since the caps 12, 14 are placed on the body 16 by sliding the caps 12, 14 laterally, there is no vertical movement which could cause accidental compression of the syringe plunger 59.

The caps 12, 14 may be secured to the body 16 by any conventional method known to those of ordinary skill in the art. In one embodiment, the caps 12, 14 are held onto the body 16 using, in part, a detent rod 28. The detent rod 28 includes a body 30, detent 32 and spring (not shown) which biases the detent 32 outwardly from the body 30. The detent rod 28 is received in a hole 34 in the syringe shield main body 16. The detent 32 is shaped to be resiliently received in a corresponding hole (not shown) in the underneath side of the caps 12, 14. Release of the caps 12, 14 from attachment with the body 16 may be accomplished by using the detent release mechanism 36 housed in the caps 12, 14. The detent release mechanism 36 may be comprised of a body 38, a button 40 and a resiliently biased rod (not shown). Depression of the button 46 pushes down on the rod engaging the detent 32 which allows the caps 12, 14 to be released from the main body 16. The detent release mechanism 36 is held in place by a plate 42 which is shaped to fit in a recess in the caps 12, 14. The plate 42 is held in place via conventional screw-type closures 44. It is to be understood that the particular method for attaching the caps 12, 14 to the body 16 described herein is a single illustrative example of one operative method. Other operative method known to those of ordinary skill in the art may be used and are considered within the scope of the present invention.

The side loading design of the injecting cap 12 allows for an injecting rod 46 to be provided in the cap 12. The injecting rod 46 may include a plunger thumb pad gripping mechanism 48 in order to facilitate the injecting of a patient with the contents of a syringe 26 located in the shield 10 without removing the syringe 26 from the shield 10 and may be used during the injecting and or filling of the syringe 26. The injecting rod 46 is preferably shaped to be slidingly received in a channel 50 in the injecting cap 12 and may include a plunger thumb pad gripping mechanism 48 located near a bottom portion thereof. The plunger thumb pad gripping mechanism 48 may be comprised of a lip 52 located at the bottom of the injecting rod 46 shaped to catch the underside of a plunger thumb gripping pad 54 and a resiliently biased downwardly sloping finger 56 positioned above and spaced apart from the lip 52 slightly wider than the width of the gripping pad 54. The finger 56 may be resiliently biased by any conventionally known mechanism such as a leaf spring, helical spring, etc. (not shown).

The injecting cap 12 also preferably includes a syringe detent mechanism 51 for holding the body portion 53 of the syringe 26 in place so that the syringe plunger 59 may be manipulated. The syringe detent mechanism 51 may be comprised of two cams 55 that are pivotally attached to a boss 63 formed in the cap 12, are resiliently biased by a pair of helical springs 57 and are shaped to engage and hold down the thumb flaps 61 on the syringe 26.

In accordance with the invention, the shield 10 preferably includes a removable needle shield apparatus 18 which allows a needle 60 and corresponding cap 62 to be removed from the syringe 26 and either be recapped or be replaced with a different needle, a connector valve, flexible tubing, etc. without removing the syringe 26 from the syringe shield 10 and while protecting a technician or other personnel from potential radiation exposure. Preferably, the needle shield apparatus 18 is designed such that it may accept a capped needle in any orientation and still be able to manipulate the needle 60 and cap 62 as desired. The needle shield apparatus 18 is preferably comprised of an outer jacket 64 that is made of a radiation dense material and includes threads 66 on the top thereof for mating with corresponding threads (not shown) in the lower portion of the body 16 of the shield 10. The thread angle of the needle shield 18 threads 66 must be chosen to exactly match the thread angle of the threads 67 of the syringe needle 60 so that when the needle shield 18 is unscrewed from the shield main body 16, the needle 60 unscrews easily from the syringe 26 and without damaging the threads thereof.

Preferably, the shield apparatus 18 includes a floating needle receiving chamber 68 therein that has a cap receiving member 70 captured in a lower portion thereof that is shaped to frictionally receive and grab the needle cap 62 and corresponding needle 60. The cap receiving member 70 may be made of any desired material, such as an elastomer (such as rubber) or other material that is capable of resiliently grabbing the cap 62 and holding it as necessary. Further, the inner cut-out of the cap receiving member 70 should be shaped as necessary to frictionally receive whatever shaped cap 62 is being used with the needle 60 and syringe 26.

The chamber 68 is preferably designed to "float" in the needle shield 18 so that it may adjust both horizontally and vertically in order to accept the needle cap 62 no matter what orientation it is placed in the needle shield 18. This horizontal and vertical floating characteristic may be achieved in any manner as is known in the art. For example, to achieve the desired vertical freedom, a collar 72 may be provided having a ledge 74 for rotatingly receiving an upper portion 76 of the chamber 68. In order to achieve the desired horizontal freedom, the collar 72 may be resiliently supported by springs 78. The chamber 68 may be held in the needle shield 18 in any manner which secures it sufficiently while still maintaining the desired horizontal and vertical freedom. For example, a collar stop 80 may be provided which is held into the upper portion of the needle shield 18 with pins 82. If such an arrangement is used, the collar 72 must be provided with slots 84 to maintain the desired vertical freedom of the collar 72.

In a preferred embodiment, the needle shield 18 is provided with an ejector assembly 86 for ejecting the needle 60 and needle cap 62 from the cap receiving member 70. The ejector assembly 86 may be comprised of a plunger rod 88 which is shaped to slide through the cap receiving member 70, a plunger button 90, and a helical spring 92 for biasing the plunger rod into a normally outward, non-ejecting position. The helical spring 92 is preferably seated between the needle shield 18 end cap 94 and a shoulder 96 machined in the outer jacket 64. The end cap 94 may be held on in any desired manner, including conventional screws 98. It should be noted that while the floating needle chamber 68 is described herein as a separate element of the needle shield 18, it is possible that this element could exist as a stand alone mechanism in a automatic dosing machine. Such an implementation of the chamber 18 is considered operative and within the scope of the present invention.

The shield 10 may be used as follows. An empty capped syringe 26 may be placed in the shield 10 main body 16 having the needle shield 18 already screwed thereto. The needle of the syringe 26 may be placed therein in any desired orientation as the needle receiving chamber 68 will float to receive it as such and the cap 62 will be caught by the cap receiving member 70 as discussed above. The cap 12 may then be slid onto the body 16 with the injecting rod 46 is placed in its fully retracted, or parked, position. During this process the cams 55 of the syringe detent mechanism 51 will rotate up slightly to engage the tops of the thumb pads 61 of the syringe body 59. Next, the injecting rod 46 is pulled upward. The downward sloping shape of the finger 56 allows the finger 56 to slide past the gripping pad 54. The lip 52 then catches the underside of the gripping pad 54 as the finger 52 resiliently biases back over the top of the pad 54 thereby trapping the pad 54 between the lip 52 and the finger 56. Once the plunger 59 pad 54 has been trapped in this manner, the plunger 59 may be manipulated as desired to either fill or empty the syringe 26 without having to remove the syringe 26 from the shield 10. The dual movements allow for the contents of the syringe 26 to be emptied and then refilled with additional liquid for rinsing of the syringe contents. The rinsing process can be repeated as often as necessary. The injecting & emptying rod 46 allows for an empty syringe to be filled from a bulk source of hazardous material, usually radioactive material and emptied.

The shield 10 may also be used to transport syringes filled with hazardous material, usually radioactive, locally around a facility or across federal and state roads since it meets or exceeds the necessary Department of Transportation (D.O.T.) guidelines. For transportation, either cap 12 or cap 14 may be utilized. Cap 14 is design primarily for transportation and cap 12 is designed for transportation and filling and emptying a syringe. The syringe shield 18 may be used to either remove the needle 60 and cap 62 or to thread a new needle and cap (or other accessory) into the syringe 26 as desired. To remove the needle 60 and cap 62 the shield 18 is simply unscrewed. To attach a new needle and cap (or other accessory) the old needle 60 and cap 62 may be removed using the ejector assembly 86 by depressing the plunger button 90 with the shield 18 inverted over an appropriate disposal/renewal container. Next, the new needle and cap (or other accessory) may be manually inserted into the shield 18 by depressing the head of the cap (or other accessory) into the needle receiving chamber 68 to be captured by the cap receiving member 70.

While there has been illustrated and described what is at present considered to be the preferred embodiment of the invention, it should be appreciated that numerous changes and modifications are likely to occur to those skilled in the art. It is intended in the appended claims to cover all those changes and modifications that fall within the spirit and scope of the present invention.

What is claimed is:

1. A radiation shielding syringe carrier comprising:
    a main body formed from a radiation dense material having a central core, said main body having a side cutout therein shaped for receiving and holding a syringe;
    a top cap formed from a radiation dense material shaped to be releasably attached to a top portion of said main body including a downwardly depending portion shaped to be slidably received in said side cutout; and
    said top cap further includes an injecting rod slidingly attached to said top cap, said injecting rod including a thumb pad gripping mechanism comprised of a lip located at the bottom of said injecting rod shaped to engage an underside of a syringe plunger thumb pad and a resiliently biased finger spaced therefrom shaped to engage a topside of a syringe plunger thumb pad to allow manipulation of said syringe plunger through manipulation of said injecting rod.

2. The radiation shielding syringe carrier of claim 1 further comprising a needle shield shaped to be releasably attached to a bottom portion of said main body and further including a core shaped to receive and surround a needle attached to a syringe received in said main body.

3. The radiation shielding syringe carrier of claim 1 further comprising a syringe detent mechanism shaped to engage and retain a syringe plunger thumb flap.

4. The radiation shielding syringe carrier of claim 3 wherein said syringe detent mechanism includes at least one resiliently biased cam shaped to engage a top portion of a syringe plunger thumb flap.

5. The radiation shielding syringe carrier of claim 2 wherein said needle shield is shaped to be threadably engaged with said main body.

6. The radiation shielding syringe carrier of claim 5 wherein the thread angle on the threads of said needle shield for threadably engaging said needle shield to said main body match the thread angle of the threads on a needle for threadably engaging a syringe.

7. The radiation shielding syringe carrier of claim 2 wherein said needle shield further comprises an outer jacket and a floating needle receiving chamber including a cap receiving member therein that is shaped to engage an end of a needle cap on a syringe.

8. The radiation shielding syringe carrier of claim 7 wherein said needle receiving chamber is resiliently biased within said outer jacket.

9. The radiation shielding syringe carrier of claim 7 wherein said cap receiving member is made from an elastomeric material.

10. The radiation shielding syringe carrier of claim 8 further comprising a collar stop having holes positioned therein for receiving pins therethrough, said collar stop being shaped to retain said needle receiving chamber in said outer jacket.

11. A radiation shielding syringe carrier comprising:
    a main body formed from a radiation dense material having a central core, said main body having a side cutout therein shaped for receiving and holding a syringe;
    a top cap formed from a radiation dense material shaped to be releasably attached to a top portion of said main body including a downwardly depending portion shaped to be slidably received in said side cutout;
    a needle shield shaped to be releasably attached to a bottom portion of said main body and further including a core shaped to receive and surround a needle attached to a syringe received in said main body; and
    said top cap further includes an injecting rod slidingly attached to said top cap, said injecting rod including a thumb pad gripping mechanism comprised of a lip located at the bottom of said injecting rod shaped to engage an underside of a syringe plunger thumb pad and a resiliently biased finger spaced therefrom shaped to engage a topside of a syringe plunger thumb pad to allow manipulation of said syringe plunger through manipulation of said injecting rod.

12. The radiation shielding syringe carrier of claim 11 further comprising a shipping cap formed from a radiation dense material shaped to be releasably attached to said top portion of said main body.

13. A radiation shielding needle shield made from a radiation dense material including an outer jacket and a floating needle receiving chamber positioned therein wherein said needle receiving chamber is resiliently biased within said outer jacket, said needle receiving chamber shaped to receive a capped needle of a syringe and having a cap receiving member therein.

14. The radiation shielding needle shield of claim 13 wherein said cap receiving member is made from an elastomeric material.

15. The radiation shielding needle shield of claim 13 further comprising a collar stop having holes positioned therein for receiving pins therethrough, said collar stop being shaped to retain said needle receiving chamber in said outer jacket.

* * * * *